United States Patent
Tang et al.

(10) Patent No.: US 12,092,616 B2
(45) Date of Patent: Sep. 17, 2024

(54) REAL-TIME MEASUREMENT SYSTEM AND MEASUREMENT METHOD FOR MECHANICAL PARAMETERS OF ROCK SLAG DURING EXCAVATION

(71) Applicant: Wuhan University, Wuhan (CN)

(72) Inventors: Xuhai Tang, Wuhan (CN); Tao Yang, Wuhan (CN); Quansheng Liu, Wuhan (CN)

(73) Assignee: Wuhan University, Wuhan (CN)

( * ) Notice: Subject to any disclaimer, the term of this patent is extended or adjusted under 35 U.S.C. 154(b) by 622 days.

(21) Appl. No.: 17/372,571

(22) Filed: Jul. 12, 2021

(65) Prior Publication Data

US 2022/0011204 A1    Jan. 13, 2022

(30) Foreign Application Priority Data

Jul. 10, 2020   (CN) .......................... 202010660600.6

(51) Int. Cl.
| | | |
|---|---|---|
| *G01N 3/06* | (2006.01) | |
| *G01N 1/34* | (2006.01) | |
| *G01N 3/08* | (2006.01) | |
| *G01N 33/24* | (2006.01) | |
| *G06N 3/08* | (2023.01) | |
| *G06T 7/00* | (2017.01) | |
| *G06T 7/40* | (2017.01) | |
| *G06T 7/90* | (2017.01) | |

(52) U.S. Cl.
CPC ............... *G01N 3/068* (2013.01); *G01N 1/34* (2013.01); *G01N 3/08* (2013.01); *G01N 33/24* (2013.01); *G06N 3/08* (2013.01); *G06T 7/0004* (2013.01); *G06T 7/40* (2013.01); *G06T 7/90* (2017.01); *G01N 2203/0647* (2013.01); *G06T 2207/20081* (2013.01); *G06T 2207/30132* (2013.01)

(58) Field of Classification Search
None
See application file for complete search history.

(56) References Cited

U.S. PATENT DOCUMENTS

2022/0146389 A1 *   5/2022   Liu .......................... E21D 9/003

FOREIGN PATENT DOCUMENTS

| CN | 108253938 A | * | 7/2018 | ............. G01C 11/02 |
|---|---|---|---|---|
| CN | 110043267 A | * | 7/2019 | ............. E21D 9/003 |
| CN | 110823737 A | * | 2/2020 | ............. B25J 19/02 |

* cited by examiner

*Primary Examiner* — Delomia L Gilliard
(74) *Attorney, Agent, or Firm* — JCIP GLOBAL INC.

(57) ABSTRACT

A real-time measurement system for mechanical parameters of rock slag during excavation includes a rock slag conveyor belt configured to convey rock slag; cleaning device, located on both sides of the rock slag conveyor belt, configured to clean the rock slag; an image acquisition device, located behind the cleaning device and on both sides and above the rock slag conveyor belt, configured to collect images of rock slag; an on-site loading device, for conducting on-site mechanical loading procedure on the rock slag to obtain on-site mechanical parameters. The on-site loading device includes a loading bottom plate, a push plate and a pressure head. The loading bottom plate is provided with a loading area. The push plate is located on the loading bottom plate and pushed by a pushing mechanism to push the rock slag.

6 Claims, 5 Drawing Sheets

REAL-TIME MEASUREMENT SYSTEM AND MEASUREMENT METHOD FOR MECHANICAL PARAMETERS OF ROCK SLAG DURING EXCAVATION

CROSS-REFERENCE TO RELATED APPLICATIONS

Pursuant to 35 U.S.C. § 119 and the Paris Convention Treaty, this application claims foreign priority to Chinese Patent Application No. 202010660600.6 filed Jul. 10, 2020, the contents of which, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, MA 02142.

BACKGROUND

The disclosure relates to the technical on-site mechanical measurement of rock slag, and specifically to a real-time measurement system and measurement method for mechanical parameters of rock slag during excavation.

With the development of tunneling machine technology, tunneling technologies such as tunnel boring machine (TBM) and shield tunneling have basically replaced traditional excavation methods. During the excavation process, damage to the blades due to over-hard rock is often encountered, as well as geological disasters such as rock bursts and landslides. To avoid geological hazards and improve the efficiency of excavation, real-time knowledge of the mechanical properties of the excavation face and the tunnel rock is required to monitor the nature of the rock slag in real time on-site.

However, in the prior art, traditional rock mechanical monitoring and testing such as point loading and borehole coring requires a lot of manual intervention and manual sampling to the laboratory for mechanic's experiments, which can cause rock disturbance and changes in water saturation, etc., during the transportation of the rock slag, which can adversely affect the measurement results.

SUMMARY

The disclosure provides a real-time measurement system and measurement method for rock slag mechanical parameters during the excavation process, which can obtain rock slag rock mechanical parameters through rock slag mechanical measurements, and provide big data support for intelligent control driving of the excavator, inversion of deep tunnel mechanical parameters, and intelligent prediction and control of rock burst.

Specifically, the real-time measurement system for mechanical parameters of rock slag during excavation comprises:
a rock slag conveyor belt configured to convey rock slag;
a cleaning device, located on both sides of the rock slag conveyor belt, configured to clean the rock slag;
an image acquisition device, located behind the cleaning device and on both sides and above the rock slag conveyor belt, configured to collect images of rock slag;
an on-site loading device, for conducting on-site mechanical loading procedure on the rock slag to obtain on-site mechanical parameters; the on-site loading device comprises a loading bottom plate, a push plate and a pressure head. The loading bottom plate is provided with a loading area; the push plate is located on the loading bottom plate and pushed by a pushing mechanism to push the rock slag; the pressure head is located above the loading area and pushed by the loading mechanism to move in a vertical direction to load the rock slag. The pressure head is set above the loading area and is pushed by the loading mechanism to move in the vertical direction for loading the rock slag. The loading bottom plate is provided with a slag fixing column, and a plurality of the rock slag fixing column drives and fixes the rock slag through a slag fixing mechanism. On-site mechanical loading procedure comprises a loading procedure, a relaxation procedure and an unloading procedure, which is cyclically performed to obtain the on-site mechanical parameters. The on-site mechanical parameters include hardness values, modulus of elasticity;
a handling device, located between the rock slag conveyor belt and the on-site loading device, configured to carry rock slag from the rock slag conveyor belt to the on-site loading device;
an indoor physical mechanical experimental device configured to conduct indoor physical mechanical experiments on the rock slag after processing by the on-site loading device to obtain experimental determination parameters of the corresponding mechanical properties of the rock slag;
a rock slag measurement system, comprising an image processing module, database and a machine learning module. The image processing module for processing the collected image information to obtain the image grayscale mean value of the rock slag, the texture feature parameters of the rock slag. The database is used to establish one-to-one mapping data samples corresponding to the images of the rock slag, the on-site mechanical parameters and the experimental determination parameters. The machine learning module is configured to establish training relationships based on the database to obtain connection coefficient matrix to generate a training model.

In a class of this embodiment, the cleaning device comprises a water lance set, two sets of the water lance sets being located on each side of the rock slag conveyor belt, each set of water lance sets comprising a plurality of water lances.

In a class of this embodiment, the image processing module comprises greyscale value processing, image enhancement processing, means value calculation and texture feature parameter extraction. The greyscale value processing converts the collected the rock slag image into gray images from color images by a weighted average method: the image enhancement processing adopts a linear filtering method to perform image enhancement processing on the gray-scale images; the greyscale value is calculated by the means value calculation to obtain the greyscale value of the image; the texture feature parameters are obtained by extracting the texture feature parameters of the rock slag.

In a class of this embodiment, the texture feature parameter extraction is carried out by GLCM algorithm to extract four texture feature parameters of rock slag image: energy, entropy, contrast and inverse differential moment.

In a class of this embodiment, on-site mechanical loading procedure comprises a loading procedure, a relaxation procedure and an unloading procedure, which is cyclically performed to obtain the on-site mechanical parameters. The on-site mechanical parameters include hardness values, modulus of elasticity.

In a class of this embodiment, the on-site loading device comprises a loading bottom plate, a push plate and a pressure head. The loading bottom plate is provided with a loading area; the push plate is located on the loading bottom plate and pushed by a pushing mechanism to push the rock slag; the pressure head is located above the loading area and pushed by the loading mechanism to move in a vertical direction to load the rock slag. The pressure head is set above the loading area and is pushed by the loading mechanism to move in the vertical direction for loading the rock slag.

In a class of this embodiment, the loading bottom plate is provided with a slag fixing column, and a plurality of the rock slag fixing column drives and fixes the rock slag through a slag fixing mechanism.

In a class of this embodiment, the experimental determination parameters comprise uniaxial compressive strength, Poisson's ratio, modulus of elasticity, and fracture development classification.

In a class of this embodiment, the machine learning module is implemented based on BP neural network, the input parameters are the image grayscale mean value, the texture feature parameters and the on-site mechanical parameters, the output parameters are the rock type, the experimental determination parameters.

A real-time measurement method for mechanical parameters of rock slag during excavation, the method comprising:

S1: conveying rock slag by the rock slag conveyor belt, cleaning the rock slag by the cleaning device, collecting images by the image acquisition device, obtaining the image grayscale mean value and texture feature parameters by the image processing module, storing images, the image grayscale mean value and texture feature parameters into the database into the database;

S2: carrying the rock slag from the rock slag conveyor belt to the on-site loading device by the handling device, obtaining the on-site mechanical parameters by the on-site mechanical loading procedure, storing the on-site mechanical parameters into the database;

S3: conducting indoor physical mechanical experiments on the rock slag processed by the indoor physical mechanical experimental device, obtaining the experimental determination parameters of the rock slag, and storing the experimental determination parameters of the rock slag into the database;

S4: establishing the one-to-one mapping data samples corresponding to the images of the rock slag, the on-site mechanical parameters and the experimental determination parameters by the database;

S5: generating a training model by the machine learning module training the image grayscale mean value, the texture feature parameter of the rock slag, the on-site mechanical parameters and the experimental determination parameters, and the input parameters are the image grayscale mean value, the texture feature parameters and the on-site mechanical parameters, the output parameters are the rock type, the experimental determination parameters.

S6: repeating the above steps to continuously improve the training model, using the training model to complete the real-time measurement of the mechanical properties of the on-site rock slag.

Compared with the prior art, the disclosure has the following advantages and beneficial effects:

1. a real-time measurement system and measurement method for mechanical parameters of rock slag during excavation described in the disclosure, compared with traditional methods of monitoring and testing rock mechanical such as point loading and borehole coring, does not require a lot of manual intervention and the device automatically collects a large amount of data.

2. traditional rock mechanical monitoring and testing methods such as point load and borehole coring can only collect a small amount of data, and the selection of sample sampling points is strongly influenced by human factors, but the disclosure can measure a large amount of rock slag on-site, and provide intelligent control driving of the tunneling machine, inversion of the deep mechanical parameters of the tunnel, and intelligent prediction and control of rock burst during the tunneling process. It also provides big data support for intelligent prediction and control of rock burst.

3. a real-time measurement system and measurement method for mechanical parameters of rock slag during excavation described in the disclosure has real-time, and with the support of big data, the disclosure can identify a large amount of rock slag on-site in real time through machine learning, and output rock type and mechanical property characteristic parameters in real time.

Figure 1:
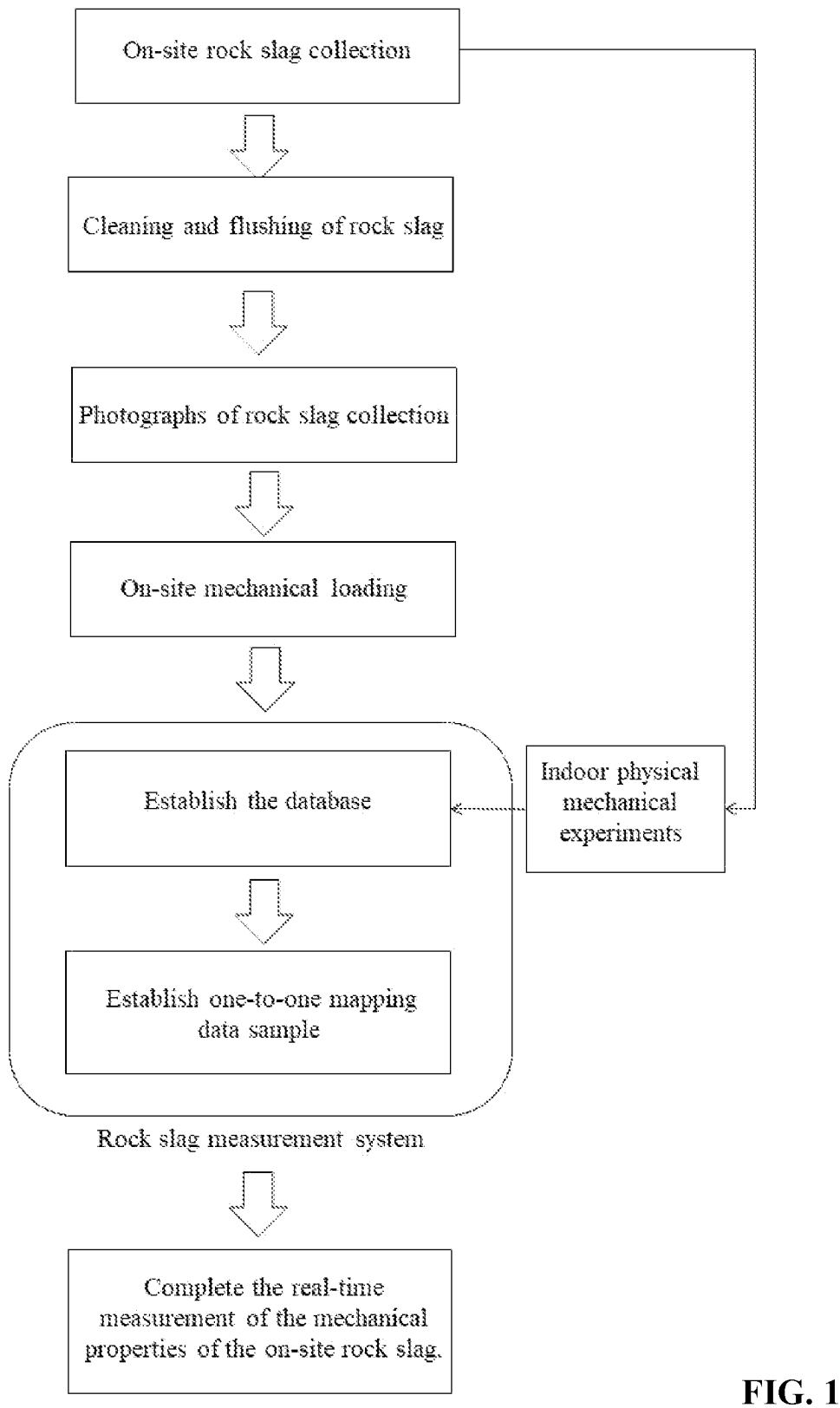
FIG. 1 shows a flow chart of the method for real-time measurement method for mechanical parameters of rock slag during excavation.

In the drawings, the following reference numbers are used: 1. Rock slag conveyor belt; 2. Cleaning device; 3. Image acquisition device; 4. Handling device; 5. On-site loading device; 6. Push plate; 7-1. First side vertical plate; 7-2. Second side vertical plate; 8. Loading bottom plate; 9. Pressure head; 10. Loading top plate; 11. Rock slag fixing column; 12. Rear movable plate; 13. Rear fixed rotation axis; 14. Rock slag; 15. Cutter; 16. Shield machine; 17. On-site inspection area point; 18. DC motor; and 19. Loading fixing column.

DETAILED DESCRIPTION

The technical solutions in embodiments of the disclosure will be clearly and completely described below in conjunction with the accompanying drawings in the embodiments of the disclosure.

In the description of the disclosure, it is understood that the terms "center", "longitudinal", "transverse", "up", "down", "front", "back", "left", "right", "vertical", "horizontal", "top", "bottom", "inside", "outside", etc. indicate an orientation or positional relationship based on the orientation or positional relationship shown in the accompanying drawings and are intended only to facilitate and simplify the description of the disclosure, not to indicate or imply that the device or element referred to must have a particular orientation, be constructed and operate in a particular orientation, and therefore are not to be construed as limiting the disclosure. Furthermore, the terms "first", "second", etc. are used for descriptive purposes only and are not to be understood as indicating or implying relative importance or as implicitly specifying the number of technical features indicated. Thus, a feature qualified with "first", "second", etc. may explicitly or implicitly include one or more such features. In the description of the invention, unless otherwise stated, "plurality" means two or more.

Figure 3:
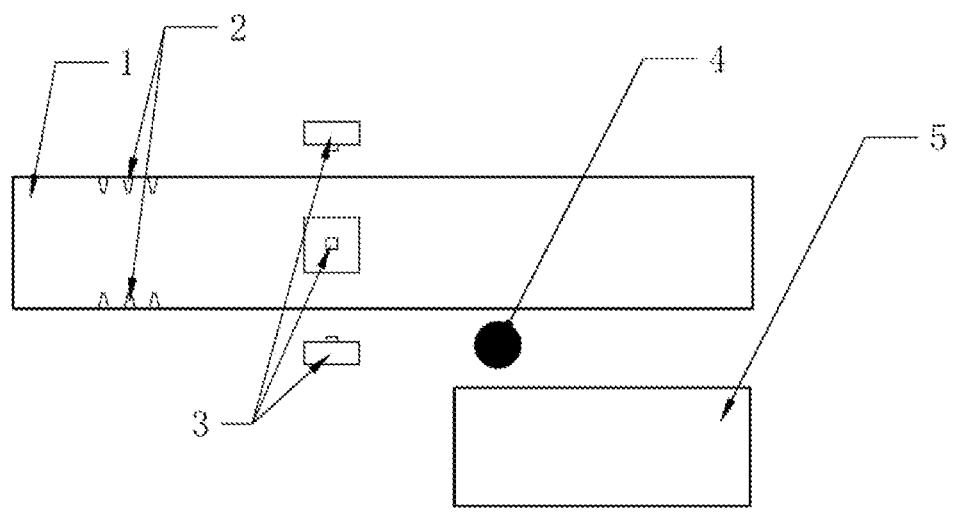
FIG. 3 shows a schematic diagram of the rock slag conveyor belt, the cleaning device, the image acquisition device, the on-site loading device and the handling device of the disclosure.

As shown in FIGS. 1 and 3, a real-time measurement system for mechanical parameters of rock slag during excavation comprises a rock slag conveyor belt 1, a cleaning device 2, an image acquisition device 3, an on-site loading device 5, a handling device 4, an indoor physical mechanical experiment device and a rock slag measurement system.

In particular, the rock slag conveyor belt 1 is used to transport the rock slag 14.

The cleaning device 2 is located on both sides of the rock slag conveyor belt 1 and is used to clean the rock slag 14.

The image acquisition device 3 is located behind the cleaning device 2 and on both sides and above the rock slag conveyor belt 1 and is used to acquire images of the rock slag 14.

The on-site loading device 5 is used for the on-site mechanical loading procedure of the rock slag 14 to obtain the on-site mechanical parameters.

The handling device 4 is located between the rock slag conveyor belt 1 and the on-site loading device 5 for conveying the rock slag 14 from the rock slag conveyor belt 1 to the on-site loading device 5.

Indoor physical mechanical experimental device for conducting indoor physical mechanical experiments on the rock slag 14 after the on-site loading device 5 has been processed to obtain the experimental determination parameters of the mechanical properties of the rock slag 14.

The rock slag measurement system comprises image processing module, database and machine learning module. The image processing module for processing the collected image information to obtain the image grayscale mean value of the rock slag, the texture feature parameters of the rock slag 14. The database is used to establish one-to-one mapping data samples corresponding to the images of the rock slag 14, the on-site mechanical parameters and the experimental determination parameters. The machine learning module is configured to establish training relationships based on the database to obtain connection coefficient matrix and generate a training model.

As shown in FIG. 3, during the process of transporting the rock slag 14 on the rock slag conveyor belt 1, the rock slag 14 is cleaned and rinsed through the cleaning device 2; Then the image of the rock slag 14 is captured through the image acquisition device 3 and the captured image is processed through the image processing module to obtain the image grayscale mean value and the texture feature parameters of the rock slag 14; The rock slag 14 is transported from the rock slag conveyor belt 1 to the on-site loading device 5 through the handling device 4. Then the on-site mechanical loading procedure is performed on the rock slag 14 through the on-site loading device 5 to obtain the on-site mechanical parameters. The rock slag 14 processed by the on-site loading device 5 is subjected to the indoor physical mechanical experiment to obtain the experimental determination parameters. Generating a training model by the machine learning module training the image grayscale mean value, the texture feature parameter, the on-site mechanical parameters and the experimental determination parameters of the rock slag 14. Repeating the above steps to continuously improve the training model.

There is no need to conduct indoor physical mechanical experiments after obtaining an improved training model with a certain accuracy rate. The image of the rock slag is acquired by the image acquisition device 3 and the image processing module is used to process the acquired image to obtain the image grayscale mean value, the texture feature parameters of the rock slag. Perform on-site mechanical loading program on the rock slag through the on-site loading device 5 to obtain the on-site mechanical parameters. Input the image grayscale mean value, the texture feature parameters, and the on-site mechanical parameters into improved training model to obtain experimental determination parameters and the type of slag which have been input to the improved training model, preventing the process of transporting the rock slag from causing rock disturbance and changes in water saturation rate, etc., which may adversely affect the measurement results.

This embodiment is based on image recognition and on-site mechanical loading to measure the physical properties of the rock, followed by precise laboratory measurements and finally by machine learning to identify the type of this rock slag based on a training model. Through this method, the staff in the on-site can carry out real-time inspection of the excavated rock sections based on the training model, combined with observation to judge the real-time inspection results to cope with the situation brought about by the different nature of the rock, and are able to carry out on-site real-time mechanical property measurement of a large number of rock slag. During the excavation process, the present invention provides big data support for intelligent control driving of the tunneling machine, inversion of the deep mechanical parameters of the tunnel, and intelligent prediction and control of rock burst.

In the disclosure, tunneling is carried out through the shield machine 16.

As shown in FIG. 3, the cleaning device 2 consists of two water lance groups, which are located on both sides of the rock slag conveyor belt 1, and each group of water lance groups comprises a plurality of water lances. In this embodiment of the invention, each group of water lances is evenly arranged with three water guns at a certain angle from top to bottom, so that the rock slag 14 can be cleaned and rinsed more comprehensively.

The image acquisition devices with cameras are fixed on the turntables, which are respectively distributed on the left, right and directly above the rock slag conveyor belt 1. The cameras collect images from the left, right and top of the rock slag conveyor belt 1. When the image acquisition device 3 detects that the rock slag 14 reaches the imaging area through the sensor, the three cameras start working at the same time to take high-speed photographs, and simultaneously collect the rock slag images from three directions, so that the collected images are more comprehensive and clear. Wherein, the sensor may be a photoelectric sensor. When the rock slag 14 reaches the imaging area, the photoelectric sensor sends a signal and controls the three cameras through the controller to start working at the same time for high-speed photography.

The processing of the image by the image processing module is described in detail below.

The image processing module comprises greyscale value processing, image enhancement processing, means value calculation and texture feature parameter extraction.

The greyscale value processing converts the collected the rock slag 14 image into gray images from color images by a weighted average method.

In the process of the image grayscale value processing, it is agreed that f(x,y) is the greyscale value of the point with coordinates (x,y) in the two-dimensional picture, R(x,y), G(x,y) and B(x,y) are the values of the point with coordinates (x,y) on the red, green and blue components. This embodiment uses the weighted average method for grayscale processing of the image as follows:

$$f(x,y)=0.30*R(x,y)+0.59*G(x,y)+0.11*B(x,y)$$

Image enhancement processing uses linear filtering methods to image smooth greyscale images. Image enhancement is one of the most important methods in image processing, optimizing image quality and providing the basis for subsequent image recognition and image processing. For example, in image diagnosis, contrast enhancement highlights important features hidden in the data and therefore reduces the gap between data estimation and objective perception.

First assume that the digital image to be processed has a greyscale level of L and that the input f(n) is the greyscale value of the target pixel, a pixel whose position in the whole image is n:

$$n=[n_1,n_2]$$

where $n_1$ and $n_2$ represent the rows and columns in which the target pixels are located, respectively.

$f_1(n), f_2(n), \ldots, f_8(n)$ represent the greyscale values of the 8 pixels adjacent to f(n), which together form a 3×3 window, i.e.:

$$0 \leq f(n) \leq L-1$$

$$0 \leq f_i(n) \leq L-1$$

where f(n) represents the greyscale value of the target pixel; $f_i(n)$ represents the greyscale value of the neighboring pixels of the target pixel; i represents the neighboring pixel ordinal number, i=1, 2, . . . , 8, output of the mean filtering algorithm is defined as follows:

$$y(n) = f(n) \oplus \frac{1}{8}\sum_{i=1}^{8}(f_i(n) - f(n))$$

where y(n) represents the greyscale scale value after processing by the filtering algorithm. where ⊕ represents the prescribed operator symbol, which is defined as follows:

$$a \oplus b = \text{MIN}\{a+b, L-1\}$$

The image grayscale mean value is calculated to obtain the image grayscale mean value, and the above grayscale values are subjected to the mean value V calculation:

$$V = \frac{1}{N \times M}\sum_{i=0}^{N-1}\sum_{j=0}^{M-1}f(i,j)$$

where N×M represents the size of the image, f(i,j) represents the greyscale value of pixel (i,j) after image enhancement; M represents the number of pixel points for the length of the image; N represents the number of pixel points for the width of the image, i=1, 2, . . . , M−1; j=1, 2, . . . , N−1.

The texture feature parameters extraction is calculated to obtain the rock slag texture feature parameters, and the rock slag texture feature parameters are extracted by the GLCM algorithm for the processed images.

Texture feature parameter extraction is achieved by extracting the rock slag texture feature parameters by GLCM algorithm, and the four image texture feature parameters of energy, entropy, contrast, and inverse difference moment are extracted.

N×M is the size of the two-dimensional rock slag 14 image, and (x,y) is the coordinate of any point in this image. The point (x,y) forms a point pair with any fixed point in the image (generally selected as a nearby point), and a movement relative to that fixed point will result in a different point pair with a greyscale scale value of $(g_1, g_2)$. The (x,y) spatial coordinates of the rock slag 14 image are greyed out to the "grey pair" (x,y) description, and the greyscale matrix of the rock slag 14 image is normalized as follows:

$$P(g_1, g_2) = \frac{N(g_1, g_2)}{R}$$

$$R = \begin{cases} N(N-1) & \theta = 0° \text{ or } \theta = 90° \\ (N-1)^2 & \theta = 45° \text{ or } \theta = 135° \end{cases}$$

where $P(g_1, g_2)$ represents the normalized probability distribution function of the greyscale scale pair, and $N(g_1, g_2)$ represents the number of occurrences of this greyscale scale pair; θ represents the angle between any point (x,y) in the image and the line connecting any fixed point in the image and the horizontal axis of the coordinate axis; N represents the number of levels of greyscale scale values, that is, N pixel points.

In order to improve the resolution efficiency of the rock slag 14 image recognition, the four parameters of energy, entropy, contrast map and inverse difference moment of GLCM are used to extract the global features of rock slag 14 image as texture feature parameters. Let G(i,j) represent the K×K-order co-occurrence matrix, G represent the commonly used features of the greyscale-level co-occurrence matrix, and the four parameters are as follows:

order co-occurrence matrix and to denote the features commonly used in the greyscale scale co-occurrence matrix, the four parameters are expressed as follows:

(1) Energy ASM: reflects the thickness of the texture of the rock slag image and the uniformity of the grayscale distribution.

$$ASM = \sum_{i=1}^{k}\sum_{j=1}^{k}(G(i,j))^2$$

Entropy value ENT: indicates the complexity of texture in the rock slag image.

$$ENT = -\sum_{i=1}^{k}\sum_{j=1}^{k}G(i,j)\lg G(i,j)$$

Contrast CON: reflects the depth of texture and groove of the rock slag image.

$$CON = \sum_{n=0}^{k-1} n^2 \left\{ \sum_{i=j=n} G(i, j) \right\}$$

Inverse difference moment IDM: reflects the homogeneity of the texture of the rock slag image, and measures the local change in the texture of the rock slag rock image.

$$IDM = \sum_{i=1}^{k} \sum_{j=1}^{k} \frac{G(i, g)}{1 + (i - j)^2}$$

A detailed description of the on-site loading device 5 and the on-site mechanical loading procedure is given below.

Figure 4:
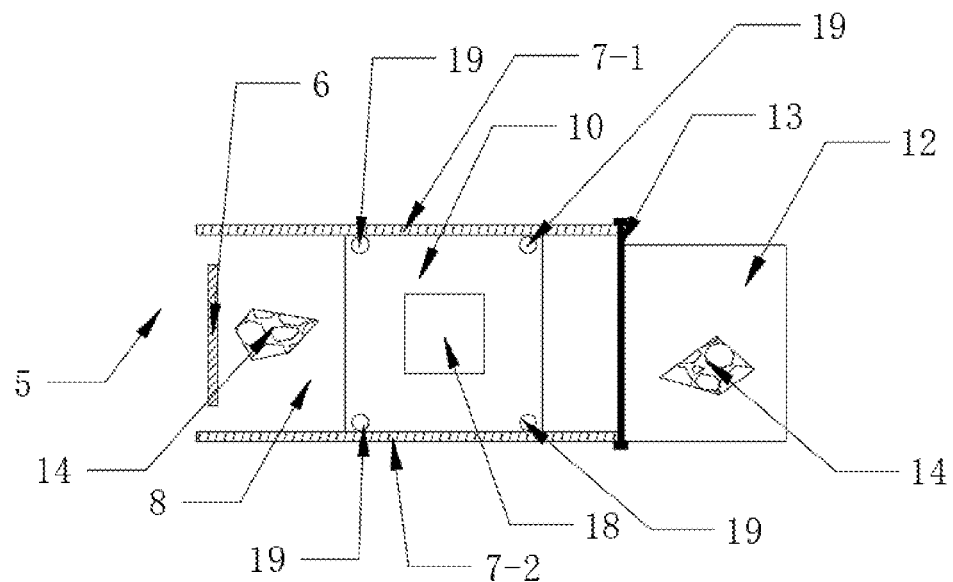
FIG. 4 shows a top view of the on-site loading device of the disclosure.
Figure 5:
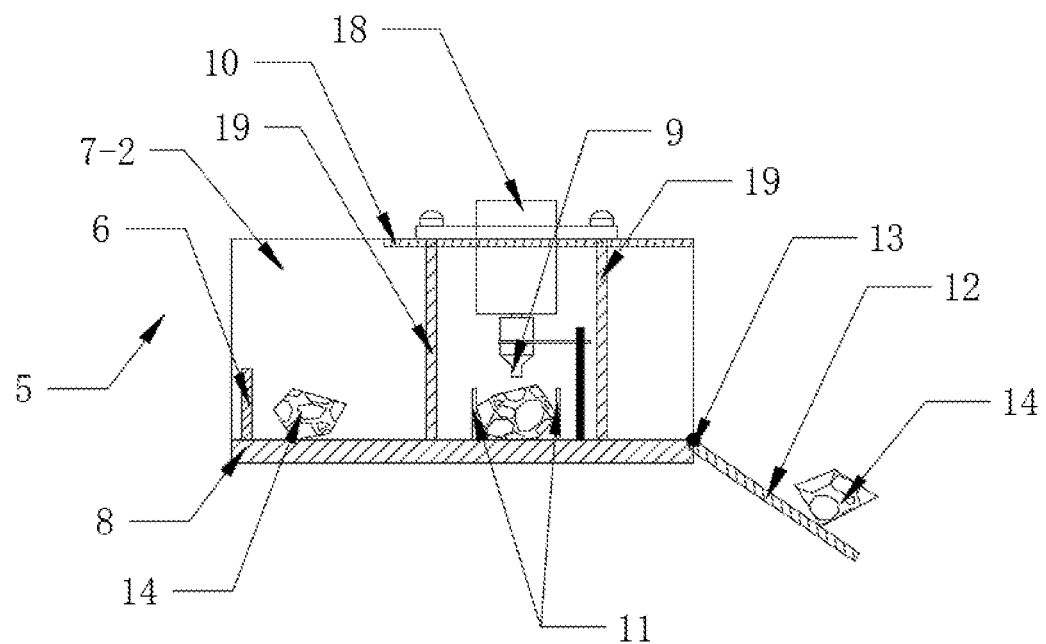
FIG. 5 shows a main view of the on-site loading device of the disclosure.
Figure 6:
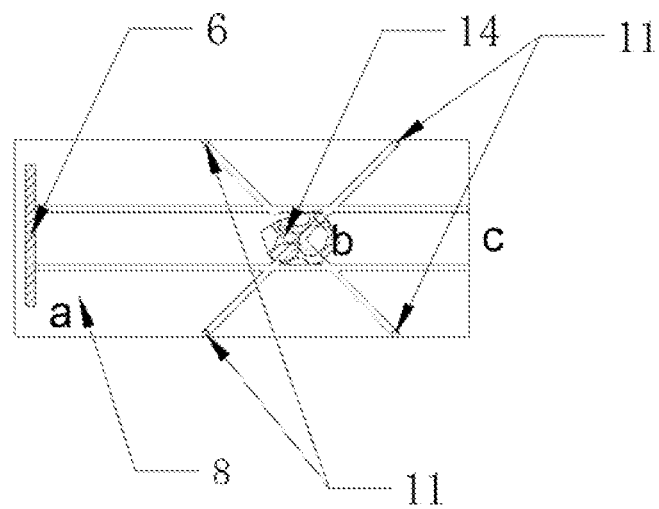
FIG. 6 shows a schematic view of the loading bottom plate, the push plate, and plurality of the rock slag fixing columns connected in the on-site loading device of the disclosure.

On-site mechanical loading procedure comprises a loading procedure, a relaxation procedure and an unloading procedure, which is cyclically performed to obtain the on-site mechanical parameters. The on-site mechanical parameters include hardness values, modulus of elasticity;

As shown in FIGS. 4-6, the on-site loading device 5 comprises a loading bottom plate 8, a push plate 6 and a pressure head 9. The loading bottom plate 8 is provided with a loading area: the push plate 6 is located on the loading bottom plate 8 and pushed by a pushing mechanism to push the rock slag: the pressure head 9 is located above the loading area and pushed by the loading mechanism to move in a vertical direction to load the rock slag. The handling device 4 places the rock slag 14 on the loading bottom plate 8, and the pushing plate 6 pushes the rock slag 14 to the loading area through a pushing mechanism.

In order to facilitate loading, a plurality of loading fixing column 19 are evenly arranged to enclose the loading area. The plurality of the rock slag fixing column 11 are used to fix the rock slag 14, and the rock slag fixing column 11 is moved by the rock slag fixing mechanism. Before the loading mechanism loads the rock slag, the rock slag fixing column 11 moves and fixes the rock slag to facilitate the loading mechanism to load the rock slag. When the loading is completed, the rock slag fixing column 11 moves to loosen the rock slag, and the push plate continues to push the rock slag.

The rock slag fixing mechanism can adopt any one of air cylinder, hydraulic cylinder, electric push rod, screw nut mechanism, and rack and pinion mechanism, as long as the rock slag fixing mechanism can be driven to move and fix the rock slag.

The pushing mechanism can adopt any one of a cylinder, a hydraulic cylinder, an electric push rod, a screw nut mechanism, and a rack and pinion mechanism, as long as the pushing plate 6 can be moved so that the rock slag 14 is pushed to the loading area.

In order to facilitate the installation of the loading mechanism, the loading bottom plate 8 is provided with the first side vertical plate 7-1 and the second side vertical plate 7-2. The loading top plate 10 is provided between the first side vertical plate 7-1 and the second side vertical plate 7-2. The loading mechanism is installed on the loading top plate 10, and the pressure head 9 is arranged on the loading mechanism, so that the pressure head 9 can move in the vertical direction to load the rock slag 14.

The loading mechanism may be a DC motor 18, which converts electrical energy into mechanical energy.

In the above-mentioned the on-site loading device 5, the on-site mechanical loading program is a cycle of loading-relaxation-unloading. Generally, the load-displacement curve during the loading process is characterized by non-linear elastoplasticity, and the purpose of the relaxation phase is to eliminate the time-related viscosity factor before unloading. The initial stage of unloading can be considered as a purely elastic recovery stage, and the curve is linear elastic. Through the experiment on the rock slag, we obtained multiple sets of values. We used the mean statistical method to process, and eliminated some obvious abnormal data, and obtained the on-site mechanical parameters of the corresponding the rock slag, including the hardness value and the elastic modulus.

Figure 7:
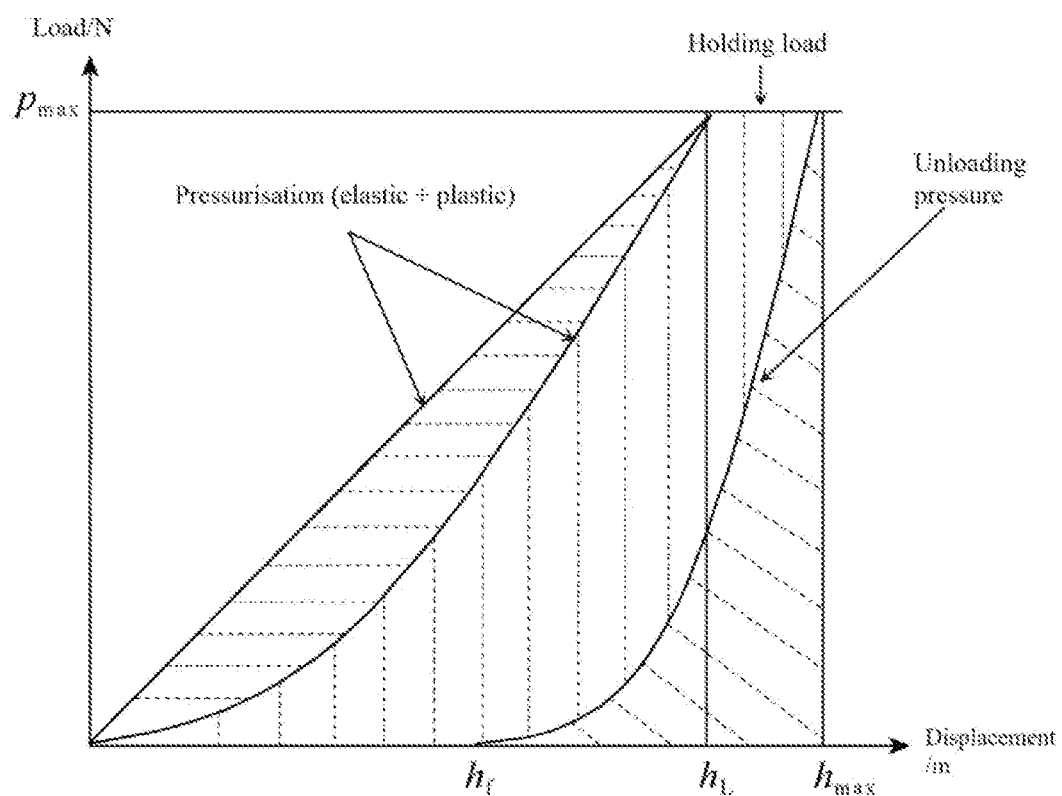
FIG. 7 shows a schematic diagram of load-displacement variation curve in the on-site mechanical loading procedure of the disclosure.

During the on-site mechanical loading procedure, after the pressure head 9 is gradually pressed into the rock slag, the material near the pressure head 9 first undergoes elastic deformation. As the load increases, the rock slag begins to undergo plastic deformation. When the pressure head 9 is unloaded, the elastic deformation is restored. As shown in FIG. 7, the load-displacement curve is drawn from the data, and the curve is used to calculate the elastic modulus and hardness of the rock. In the figure: $h_f$ represents a residual depth, $h_l$ represents starting displacement at the point of load retention, $h_{max}$ represents maximum displacement. The hardness H is calculated by the formula:

$$H = \frac{p_{max}}{A_c}$$

$$A_c = 24.5 h_c^2$$

where $P_{max}$ represents the maximum loading pressure, $A_c$ represents the projected area of contact under the corresponding load and $h_c$ represents the contact depth.

Where $h_c$ is related to $h_{max}$ as follows:

$$h_{max} - h_c = \varepsilon \frac{p_{max}}{S}$$

$$h_c = \frac{2(v_E - 1)}{2v_E - 1} h_{max}$$

where, $h_{max}$ represents maximum displacement, S represents contact stiffness. ε is a constant, 0.75, $v_E$ represents elastic energy ratio, unfactored;

Once the contact projection area and contact depth have been obtained, the discounted modulus of elasticity $E_r$ can be calculated by the following equation:

$$E_r = \frac{\sqrt{\pi} S}{2\beta \sqrt{A_c}}$$

where β represents a constant associated with the geometry of the indenter 9;

The discounted modulus of elasticity can be used to reflect the compound elastic deformation of the pressure head 9 and the specimen and can be translated into the true modulus of elasticity of the specimen by calculating the expression:

$$\frac{1}{E_r} = \frac{1-v^2}{E} + \frac{1-v_i^2}{E_i}$$

where v represents the Poisson's ratio of the specimen, uncaused; $v_i$ represents the Poisson's ratio of the pressure head 9, a constant; and $E_i$ represents the modulus of elasticity of the indenter, a constant.

As one of the embodiments, as shown in FIG. 5. The rear movable plate 12 is arranged on one side of the loading bottom plate 8, and the rear movable plate 12 is hinged with the loading bottom plate 8 through the rear fixed rotation axis 13. When the loading is completed, the rock slag fixed column 11 moves to loosen the rock slag 14 and the push plate 6 continues to push the rock slag 14 to the rear movable plate 12. After the rock slag 14 is collected by the rear movable plate 12, the rear fixed rotation axis 13 is driven to rotate by a motor, which in turn drives the rear movable plate 12 to rotate and tilt, causing the rock slag 14 to fall to a collecting device. The collected rock slag can be further used in door physical mechanical experimental device to obtain experimental determination parameters of the rock slag 14. The experimental determination parameters obtained by the indoor physical mechanical experimental device are more abundant and accurate than the data measured on-site.

The experimental determination parameters in the indoor physical mechanical experiments comprise uniaxial compressive strength $\sigma_c$, Poisson's ratio μ, modulus of elasticity E, and fracture development classification $C_r$.

Figure 8:
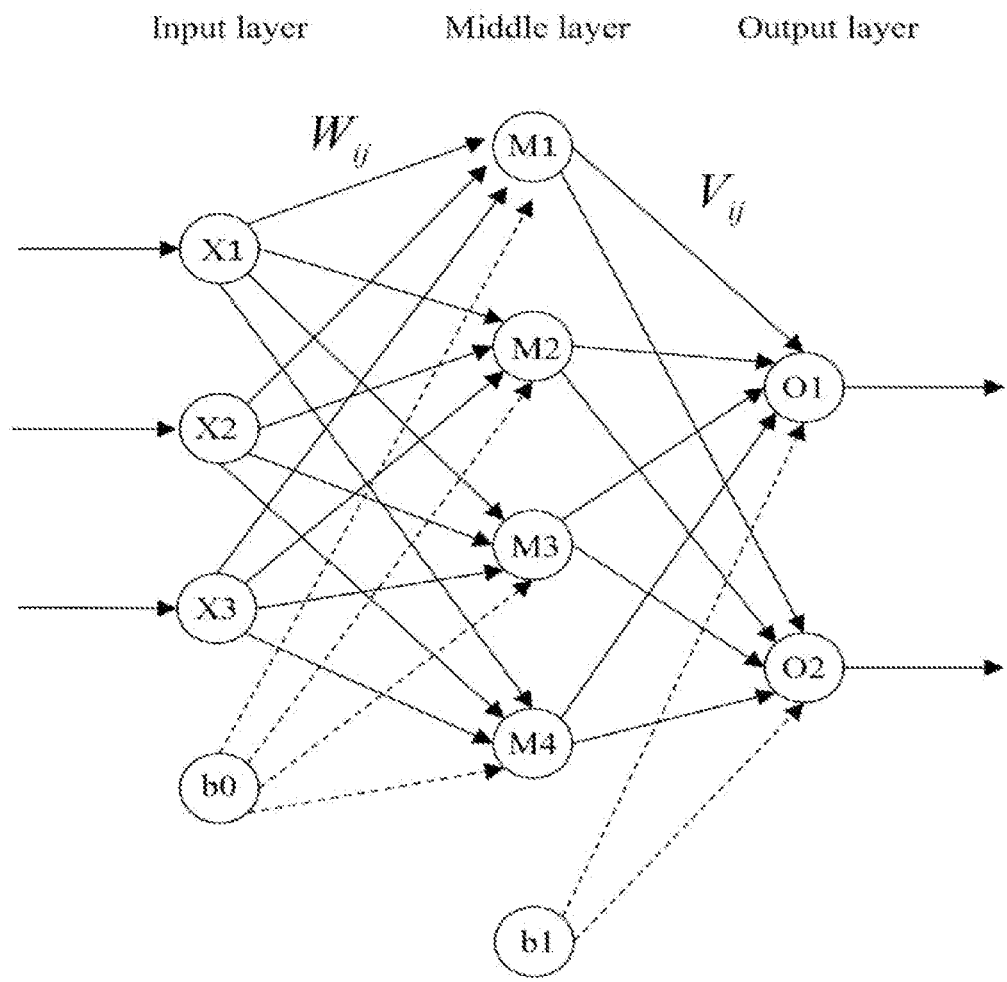
FIG. 8 shows a schematic diagram of the structure of the BP neural network in the machine learning module of the disclosure.

A detailed description is given below with reference to the creation of the training model in FIG. 8.

The machine learning module is implemented based on BP neural network. The input parameters are the image grayscale mean value, the texture feature parameters of the rock slag, on-site mechanical loading procedure, and the output parameter are the rock type and the experimental determination parameters. The network is divided into two stages, training and testing, as follows:

The unit weight W of the input layer, middle layer and output layer of the network is normalized, which take usually a random value between [−1.0~1.0]. The first layer is the input layer, containing three neurons $X_1$, $X_2$, $X_3$ and an intercept of N. The second layer is the hidden layer, containing four neurons $M_1$, $M_2$, $M_3$, $M_4$ and an intercept of $b_1$. The third layer is the output layer, containing two neurons $O_1$, $O_2$. $W_{ij}$ is the weight value from the input layer to the hidden layer and $V_{ji}$ is the weight value from the hidden layer to the output layer. The intercepts $b_0$ and $b_1$ can be determined experimentally and are usually taken to be (1.0-5.0). Each node is operated using an activation function.

(1) For forward propagation:
Input layer to intermediate layer.

$$M_i = \left(\sum_{j=0}^{3} W_{ij} \cdot X_j + b_0\right)$$

Where $W_{ij}$ denotes the weight value from the input layer to the intermediate layer; $X_j$ denotes the neurons in the input layer, j=1, 2, 3; $M_i$ denotes the neurons in the intermediate layer, i=1, 2, 3, 4; and the $b_0$ denotes the intercept of the input layer;

If the Sigmoid function is used for the activation function, the output of the neural network $M_i$ is $out_{Mi}$:

$$out_{Mi}=1/(1+e^{-M_i})$$

Intermediate layer to output layer:

$$O_j = \left(\sum_{j=0}^{3} V_{ji} \cdot out_{Mi} + b_1\right)$$

Where $V_{ji}$ denotes the weight value from the intermediate layer to the output layer and $b_1$ denotes the intercept of the intermediate layer.

Using the activation function, the output $out_{oj}$ of $O_j$ is calculated as:

$$out_{Oj}=1/(1+e^{-O_j})$$

(2) For back propagation.
target is noted as the target value; output is noted as the actual output value, with an overall error of $E_{total}$:

$$E_{total}=\Sigma\tfrac{1}{2}(target-output)^2$$

Updating of weight values $W_{ij}$, $V_{ji}$ weights:

$$W_{ij}^+ = W_{ij} - u \cdot e_{ij}$$

$$V_{ji}^+ = V_{ji} - u \cdot d_{ji}$$

Where u refers to the learning efficiency and u is taken as (0-1.0), and the number of partial layers $e_{ij}$ and $d_{ji}$ are:

$$e_{Mi} = \frac{\partial E_{total}}{\partial W_{ij}}$$

$$e_{ji} = \frac{\partial E_{total}}{\partial V_{ji}}$$

The provided mapped data samples are used as input for training and learning until the convergence conditions are met; the mapped data samples are then continued to be input and the cycle continues until enough samples are input and the connection coefficient matrix is stored. The new samples in the on-site are tested for identification by the connection coefficient matrix established.

The image information such as color and the texture feature parameters of the rock slag 14 and the on-site mechanical parameters is first displayed in image form in the 3D platform in the server data space, and the information is counted numerically and the statistical data graphs are output. After deriving the information of the rock slag 14, the 3D platform transmits the above data to the server slag measurement system in real time. The server slag measurement system identifies the information of rock slag 14 received by the server through the training relationship established by the BP neural network, thus outputting the type and mechanical properties of rock slag 14.

Traditional rock mechanics monitoring and testing methods such as point load and borehole coring can only collect a small amount of data, and the selection of sample sampling points is strongly influenced by human factors, but the disclosure can measure a large amount of rock slag on-site, and provide intelligent control driving of the tunneling machine, inversion of the deep mechanical parameters of the tunnel, and intelligent prediction and control of rock burst during the tunneling process. It also provides big data support for intelligent prediction and control of rock burst.

As one of the embodiments, the preliminary restoration of the rock mechanical property state of the cavern based on the on-site measurement results is preliminarily achieved by the following.

Figure 2:
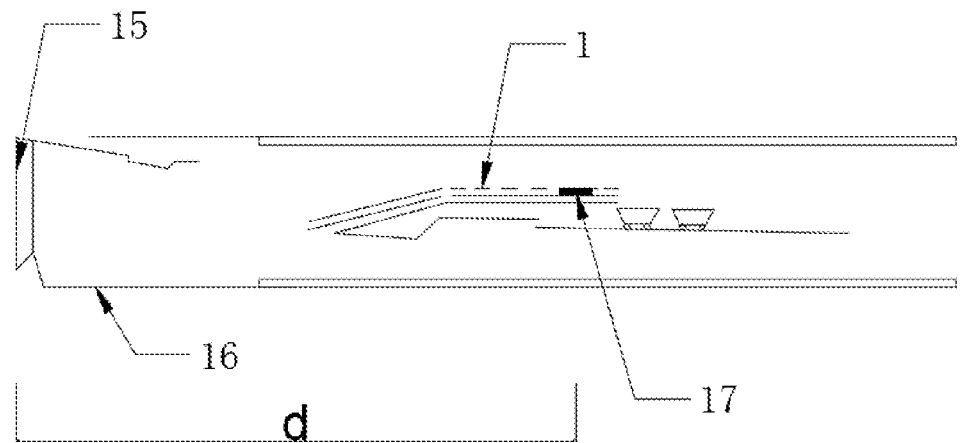
FIG. 2 shows a schematic diagram of the tunneling of the shield machine of the disclosure.

As in FIG. 2, after the cutter 15 works, the rock slag is generated at the front end of the shield machine 16 and transported to the on-site inspection zone point 17 via the rock slag conveyor belt 1. The on-site inspection zone point 17 is provided with the image acquisition device 3, the distance between the front end of the shield machine 16 and the on-site inspection zone point 17 is d. F represents the state of rock mechanical properties of the entire cavern chamber at a certain location, and S represents the rock slag mechanical data parameters detected on-site at a certain location and identified by machine learning, then we have:

$$F(x)=S(x+d)$$

A real-time measurement method for mechanical parameters of rock slag during excavation, comprising:
- S1: Conveying rock slag by the rock slag conveyor belt 1, cleaning the rock slag by the cleaning device 2, collecting images by the image acquisition device 3, obtaining the image grayscale mean value and texture feature parameters by the image processing module, storing images, the image grayscale mean value and texture feature parameters into the database;
- S2: Carrying the rock slag from the rock slag conveyor belt 1 to the on-site loading device 5 by the handling device 4, obtaining the on-site mechanical parameters by the on-site mechanical loading procedure, storing the on-site mechanical parameters into the database;
- S3: Conducting indoor physical mechanical experiments on the rock slag processed by the indoor physical mechanical experimental device 5, obtaining the experimental determination parameters of the rock slag, and storing the experimental determination parameters of the rock slag into the database;
- S4: Establishing the one-to-one mapping data samples corresponding to the images of the rock slag, the on-site mechanical parameters and the experimental determination parameters by the database;
- S5: Generating a training model by the machine learning module training the image grayscale mean value, the texture feature parameter of the rock slag, the on-site mechanical parameters and the experimental determination parameters, and the input parameters are the image grayscale mean value, the texture feature parameters and the on-site mechanical parameters, the output parameters are the rock type, the experimental determination parameters.
- S6: Repeating the above steps to continuously improve the training model, using the training model to complete the real-time measurement of the mechanical properties of the on-site rock slag.

In step 5 above, establish the one-to-one mapping data samples corresponding to the images of the rock slag, the on-site mechanical parameters and the experimental determination parameters by the database. Complete the neural network training based on the one-to-one mapping data samples, obtain the connection coefficient matrix, establish the training model, and obtain the slag measurement system. The training model uses a continuously trained BP neural network structure, the input parameters are the image grayscale mean value, the texture feature parameters and the on-site mechanical parameters, the output parameters are the rock type, the experimental determination parameters.

Real-time determination of the nature of the on-site slag: the identification of the on-site slag by the rock slag measurement system, real-time output of the rock type and mechanical properties of the rock slag experimental determination parameters, including uniaxial compressive strength $\sigma_c$, Poisson's ratio $\mu$, modulus of elasticity E, fracture development degree classification $C_r$, hardness H, etc. And based on the monitoring and identification data preliminary reduction of the cavern rock mechanical properties state.

The disclosure is real-time in nature. With the support of big data, the disclosure is able to identify a large amount of rock slag on-site in real time through machine learning and output rock type and mechanical property characteristic parameters in real time.

It will be obvious to those skilled in the art that changes and modifications may be made, and therefore, the aim in the appended claims is to cover all such changes and modifications.

What is claimed is:

1. A real-time measurement system for mechanical parameters of rock slag during excavation, the system comprising:
   a rock slag conveyor belt configured to convey rock slag;
   a cleaning device, located on both sides of the rock slag conveyor belt, configured to clean the rock slag;
   an image acquisition device, located behind the cleaning device and on both sides and above the rock slag conveyor belt, configured to collect images of rock slag, the images are two-dimensional images;
   an on-site loading device, for conducting on-site mechanical loading procedure on the rock slag to obtain on-site mechanical parameters; wherein the on-site loading device comprises a loading bottom plate, a push plate and a pressure head; the loading bottom plate is provided with a loading area; the push plate is located on the loading bottom plate and pushed by a pushing mechanism to push the rock slag; the pressure head is located above the loading area and pushed by the loading mechanism to move in a vertical direction to load the rock slag; the pressure head is set above the loading area and is pushed by the loading mechanism to move in the vertical direction for loading the rock slag; the loading bottom plate is provided with a slag fixing column, and a plurality of the rock slag fixing column drives and fixes the rock slag through a slag fixing mechanism; on-site mechanical loading procedure comprises a loading procedure, a relaxation procedure and an unloading procedure, which is cyclically performed to obtain the on-site mechanical parameters; the on-site mechanical parameters include hardness values, modulus of elasticity; a bottom of the pressure head used in the on-site loading device is cylindrical; a loading surface plus the pressure head is flat; a load-displacement curve during the loading procedure is characterized by nonlinear elastoplasticity, and a purpose of a relaxation phase is to eliminate a time-related viscosity factor before unloading, an initial stage of unloading can be considered as a purely elastic recovery stage, through an experiment on the rock slag, obtaining multiple sets of values, using a mean statistical method to process, and eliminated obvious abnormal data, the load-displacement curve is drawn from the data, and the load-displacement curve is used to calculate the modulus of elasticity and the hardness values of the rock slag, during the experiment, after the pressure head is gradually pressed into the rock slag, a material near the pressure head first undergoes elastic deformation, as a load increases, the rock slag begins to undergo plastic deformation, when the pressure head is unloaded, the elastic deformation is restored, wherein a calculation formula of a hardness H and a projected area of contact under the corresponding load $A_c$ is:

$$H = \frac{P_{max}}{A_c}$$

$$A_c = 24.5 h_c^2$$

in the formula, $P_{max}$ represents a maximum loading pressure, and $h_c$ represents a contact depth;
where $h_c$ is related to $h_{max}$ as follows:

$$h_{max} - h_c = \varepsilon \frac{P_{max}}{S}$$

$$h_c = \frac{2(v_E - 1)}{2v_E - 1} h_{max}$$

in the formula, $h_{max}$ represents a maximum displacement, S represents a contact stiffness, $\varepsilon$ is a constant, 0.75, $v_E$ represents an elastic energy ratio, unfactored;
once the projected area of contact under the corresponding load $A_c$ and the contact depth $h_c$ have been obtained, a discounted modulus of elasticity $E_r$ can be calculated by following equation:

$$E_r = \frac{\sqrt{\pi} S}{2\beta \sqrt{A_c}}$$

in the formula, $\beta$ represents a constant associated with a geometry of the pressure head;
the discounted modulus of elasticity can be used to reflect a compound elastic deformation of the pressure head and the rock slag, and can be translated into a true modulus of elasticity of the rock slag by calculating expression:

$$\frac{1}{E_r} = \frac{1 - v^2}{E} + \frac{1 - v_i^2}{E_i}$$

wherein, $v$ represents a Poisson's ratio of the rock slag, uncaused; $v_i$ represents the Poisson's ratio of the pressure head, a constant; and $E_i$ represents the modulus of elasticity of the pressure head, a constant;
a handling device, located between the rock slag conveyor belt and the on-site loading device, configured to carry rock slag from the rock slag conveyor belt to the on-site loading device;
an indoor physical mechanical experimental device configured to conduct indoor physical mechanical experiments on the rock slag after processing by the on-site loading device to obtain experimental determination parameters of the corresponding mechanical properties of the rock slag; and
a rock slag measurement system, comprising an image processing module, database and a machine learning module; wherein the image processing module is configured to process collected image information to obtain an image grayscale mean value of the rock slag and the texture feature parameters of the rock slag; the database is used to establish one-to-one mapping data samples corresponding to the images of the rock slag, the on-site mechanical parameters and the experimental determination parameters; the machine learning module is configured to establish training relationships based on the database to obtain connection coefficient matrix and generate a training model; there is no need to conduct the indoor physical mechanical experiments after obtaining the training model, the machine learning module is implemented based on a BP neural network to build an association model between the on-site mechanical parameters and the indoor physical mechanical experiments, the database is obtained through long term construction, input parameters are the image grayscale mean value, texture feature parameters of the rock slag, and the on-site mechanical parameters, and output parameter are a rock type and the experimental determination parameters; the network is divided into two stages, training and testing, as follows:
an unit weight W of an input layer, an intermediate layer and an output layer of the network is normalized, which take a random value between [−1.0~1.01; a first layer is the input layer, containing three neurons $X_1$, $X_2$, $X_3$ and an intercept of $b_o$; a second layer is a hidden layer, containing four neurons $M_1$, $M_2$, $M_3$, $M_4$ and an intercept of $b_1$; a third layer is the output layer, containing two neurons $O_1$, $O_2$; $W_{ij}$ is a weight value from the input layer to the hidden layer and $V_{ji}$ is the weight value from the hidden layer to the output layer; the intercepts $b_o$ and $b_1$ can be determined experimentally and are usually taken to be (1.0-5.0); each node is operated using an activation function;
for forward propagation:
the input layer to the intermediate layer:

$$M_i = \left( \sum_{j=0}^{3} W_{ij} \cdot X_j + b_0 \right)$$

wherein $W_{ij}$ denotes the weight value from the input layer to the intermediate layer; $X_j$ denotes the neurons in the input layer, i=1, 2, 3; $M_i$ denotes the neurons in the intermediate layer, i=1, 2, 3, 4; and the $b_o$ denotes the intercept of the input layer;
if a Sigmoid function is used for the activation function, the output of the neural network $M_i$ is $out_{Mi}$:

$$out_{Mi} = 1/(1+e^{-M_i})$$

the intermediate layer to the output layer:

$$O_j = \left( \sum_{j=0}^{3} V_{ji} \cdot out_{Mi} + b_i \right)$$

wherein $V_{ji}$ denotes the weight value from the intermediate layer to the output layer, and $b_1$ denotes the intercept of the intermediate layer;
using the activation function, the output $out_{oj}$ of $O_j$ is calculated as:

$$out_{Oj} = 1/(1+e^{-O_j})$$

for back propagation:

target is noted as a target value; output is noted as an actual output value, with an overall error of $E_{total}$:

$$E_{total} = \sum \frac{1}{2}(\text{target} - \text{output})^2$$

updating of weight values $W_{ij}$, $V_{ji}$ weights:

$$W_{ij}^+ = W_{ij} - u \cdot e_{ij}$$

$$V_{ji}^+ = V_{ji} - u \cdot d_{ji}$$

wherein u refers to a learning efficiency and u is taken as (0–1.0), and a number of partial layers $e_{ij}$ and $d_{ji}$ are:

$$e_{Mi} = \frac{\partial E_{total}}{\partial W_{ij}}$$

$$e_{ji} = \frac{\partial E_{total}}{\partial V_{ji}}$$

the provided mapping data samples are used as the input for training and learning until a convergence conditions are met; the mapping data samples are then continued to be input and a cycle continues until enough samples are input and the connection coefficient matrix is stored, new samples in the on-site are tested for identification by the connection coefficient matrix established.

2. The system of claim 1, wherein the image processing module comprises greyscale value processing, image enhancement processing, means value calculation and texture feature parameter extraction;
wherein:
the greyscale value processing converts the collected the rock slag image into gray images from color images by a weighted average method;
the image enhancement processing adopts a linear filtering method to perform image enhancement processing on the gray-scale images;
the greyscale value is calculated by the means value calculation to obtain the greyscale value of the image; and
the texture feature parameters are obtained by extracting the texture feature parameters of the rock slag.

3. The system of claim 2, wherein the texture feature parameter extraction is carried out by gray-level co-occurrence matrix (GLCM) algorithm to extract four texture feature parameters of rock slag image: energy, entropy, contrast and inverse differential moment.

4. The system of claim 1, wherein the experimental determination parameters comprises uniaxial compressive strength, Poisson's ratio, modulus of elasticity, and fracture development classification.

5. A real-time measurement method for mechanical parameters of rock slag during excavation, using the real-time measurement system for mechanical parameters of rock slag during excavation of claim 1, the method comprising:
S1: conveying rock slag by the rock slag conveyor belt, cleaning rock slag by the cleaning device, collecting images by the image acquisition device, obtaining the image grayscale mean value and texture feature parameters by the image processing module, storing images, the image grayscale mean value and texture feature parameters into the database;
S2: carrying the rock slag from the rock slag conveyor belt to the on-site loading device by the handling device, obtaining the on-site mechanical parameters by the on-site mechanical loading procedure, storing the on-site mechanical parameters into the database;
S3: conducting indoor physical mechanical experiments on the rock slag processed by the indoor physical mechanical experimental device, obtaining the experimental determination parameters of the rock slag, and storing the experimental determination parameters of the rock slag into the database;
S4: establishing the one-to-one mapping data samples corresponding to the images of the rock slag, the on-site mechanical parameters and the experimental determination parameters by the database;
S5: generating a training model by the machine learning module training the image grayscale mean value, the texture feature parameter of the rock slag, the on-site mechanical parameters and the experimental determination parameters, and the input parameters are the image grayscale mean value, the texture feature parameters and the on-site mechanical parameters, the output parameters are the rock type, and the experimental determination parameters; and
S6: repeating the above steps to continuously improve the training model, using the training model to complete the real-time measurement of the mechanical properties of the on-site rock slag.

6. The system of claim 1, wherein the cleaning device comprises a water lance set, two sets of the water lance sets being located on each side of the rock slag conveyor belt, each set of water lance sets comprising a plurality of water lances.

* * * * *